United States Patent [19]

Moon

[11] 4,230,100

[45] Oct. 28, 1980

[54] CHIROPRACTIC TABLE

[76] Inventor: Derryl E. Moon, Fairmount, N. Dak. 58030

[21] Appl. No.: 927,961

[22] Filed: Jul. 26, 1978

[51] Int. Cl.$^3$ .............................................. A61F 5/00

[52] U.S. Cl. .......................................... 128/70; 128/73

[58] Field of Search ...................... 128/69, 70, 71, 72, 128/73, 74

[56] References Cited

U.S. PATENT DOCUMENTS

| | | | |
|---|---|---|---|
| 2,262,271 | 11/1941 | De Camp | 128/74 |
| 2,630,800 | 3/1953 | Voss et al. | 128/73 |
| 3,092,102 | 6/1963 | Thompson | 128/70 |
| 4,050,454 | 9/1977 | Ekholm | 128/70 |

*Primary Examiner*—Robert W. Michell
*Assistant Examiner*—Arthur S. Rose
*Attorney, Agent, or Firm*—Zarley, McKee, Thomte, Voorhees & Sease

[57] ABSTRACT

The chiropractic table of the present invention includes a base frame, an intermediate frame above the base frame, and a table frame above the intermediate frame. A plurality of independently movable support pieces are mounted to the table frame and extend above the table frame to provide a support surface for the patient. The table may be tilted about a horizontal axis from a horizontal position to a near vertical position. It may also be elevated or lowered when in its horizontal position. One or more of the support pieces include a cock and drop feature which permits the chiropractor to elevate the piece to a predetermined height. The chiropractor then places downward pressure on the patient at a point directly above the support piece which has been elevated. A system of cams and cam followers holds the elevated piece in its upper position until the pressure reaches a predetermined magnitude, at which time the support piece is released and drops to its original position. The thoracic support piece is tilted about a horizontal axis at its middle, and includes a cock and drop feature at each of its opposite ends. The table also includes an arm rest which is movable beyond one end of the table to provide a knee rest when desired. The table also includes a continually adjustable face or head piece.

3 Claims, 18 Drawing Figures

CHIROPRACTIC TABLE

BACKGROUND OF THE INVENTION

This invention relates to a chiropractic table.

Chiropractors in the treatment of their patients require a particular type of table which permits them to manipulate the various parts of the patient's anatomy. These tables conventionally include a plurality of support pieces for the chest, head, thorax, pelvis, and tibia. Each of these support pieces is independently adjustable vertically and longitudinally so as to accommodate the particular needs of the patient and the particular size of the patient.

In the treatment of the patient, the chiropractor often exerts considerable pressure and leverage on the various portions of the patient's anatomy. This requires that the patient be placed in a position which is convenient to the chiropractor in order that the proper pressures may be applied. Therefore, it is desirable to be able to raise and lower the table to the height which is most advantageous for the chiropractor's purposes.

It is also desirable to be able to tilt the table to a near vertical position so that the patient may lean against the table and then be lowered to a horizontal position.

One feature which is desirable for various techniques of the chiropractor is the ability of the individual support pieces to be cocked and dropped. That is, the particular support piece is elevated to a predetermined position with respect to the other support pieces. The chiropractor then places downward pressure on the patient above the elevated support piece, and increases the pressure to a predetermined magnitude at which time the pelvic piece releases and drops to its original position with a sudden dropping action.

It is also desirable to have a continuously adjustable face piece for the patient so that the table may be adjusted to the proper position. Arm rests for the patient are also necessary, and occasionally there is need for a knee rest so that the patient can kneel on the knee rest and lean over the table during certain manipulative techniques applied by the chiropractor. A cervical chair is also a desirable accessory to have with the table.

SUMMARY OF THE INVENTION

The present invention utilizes an elevating mechanism which permits the table to be elevated from ground level to as high as 30 inches. The mechanism utilizes a plurality of links which are interconnected between a pedestal frame and an intermediary frame. When the links are expanded, the intermediary frame elevates with respect to the pedestal frame, and maintains its horizontal parallel relationship to the pedestal frame.

The present invention also utilizes a table frame which is mounted above the intermediary frame, and which is tiltable about a horizontal axis from a horizontal position to a position which approaches vertical. Both the tilt mechanism and the elevating mechanism are operated by a single motor or power means which is mounted within the pedestal frame.

Several of the support pieces also utilize a cock and drop feature which permits the piece to be elevated, but which permits it to drop in response to the application of a predetermined magnitude of downward pressure. The release feature is provided by a pivoting cam which has a notch therein for receiving a cam follower. The cam follower is connected to a solenoid, and the solenoid is adapted to release in response to a predetermined amount of pressure. The downward pressure exerted by the chiropractor on the support piece is translated to the cam which has a tendency to pivot so as to remove the cam follower from the notch in the cam. When the tendency to rotate becomes sufficiently great, the cam follower rolls out of the notch, the cam rotates, and the support piece drops.

The thoracic support piece utilized with the present invention has a cock and drop feature at opposite ends thereof, and has a pivotal axis intermediate its opposite ends. Thus, as the cock and drop feature at one end of the thoracic piece is operated, pivotal movement takes place about the intermediate axis of the thoracic piece. The use of such a pivotal feature on the thoracic piece eliminates the need for a lumbar piece which is often added to this type of table.

The face and head support pieces of the present invention include means for continuous adjustment so that they may be adjusted to accommodate the particular needs of the patient. Similarly, arm rests are provided adjacent the patients's arms for supportiing the patient's arms during treatment by the chiropractor. These arm rests may be pivoted beyond the end of the table to provide knee rests in the event that the patient is required to kneel during treatment.

Therefore, a primary object of the present invention is the provision of an improved chiropractic table.

A further object of the present invention is the provision of a chiropractic table which has an improved elevating mechanism.

A further object of the present invention is the provision of a chiropractic table having an improved tilt mechanism.

A further object of the present invention is the provision of a chiropractic table having an improved cock and drop feature for the various support pieces.

A further object of the present invention is the provision of a thoracic support piece which has the ability to swing about a pivotal axis intermediate its length, and which includes cock and drop mechanisms at the opposite ends thereof.

A further object of the present invention is the elimination of the need for a separate lumbar support piece.

A further object of the present invention is the provision of a chiropractic table having an infinitely adjustable face and head piece.

A further object of the present invention is the provision of a chiropractic table having arm rests which may be converted to knee pads.

A further object of the present invention is the provision of a chiropractic table having a pelvic support piece which may be elevated to various predetermined positions prior to dropping.

A further object of the present invention is the provision of a chiropractic table which is compact and efficient.

A further object of the present invention is the provision of a chiropractic table which permits the chiropractor to use various techniques while treating the patient and which will accommodate patients ranging in size from small children to large adults.

A further object of the present invention is the provision of a chiropractic table which includes a wide variety of adjustments and a long trouble free life.

A further object of the present invention is the provision of a chiropractic table having a cervical chair which can be swung to either side to allow for easy cervical adjusting.

A further object of the present invention is the provision of a device which is economical to manufacture, durable in use, and refined in appearance.

DETAILED DESCRIPTION OF THE PREFERRED EMBODIMENT

Figures 1, 2, 3, 4, 14, 15:
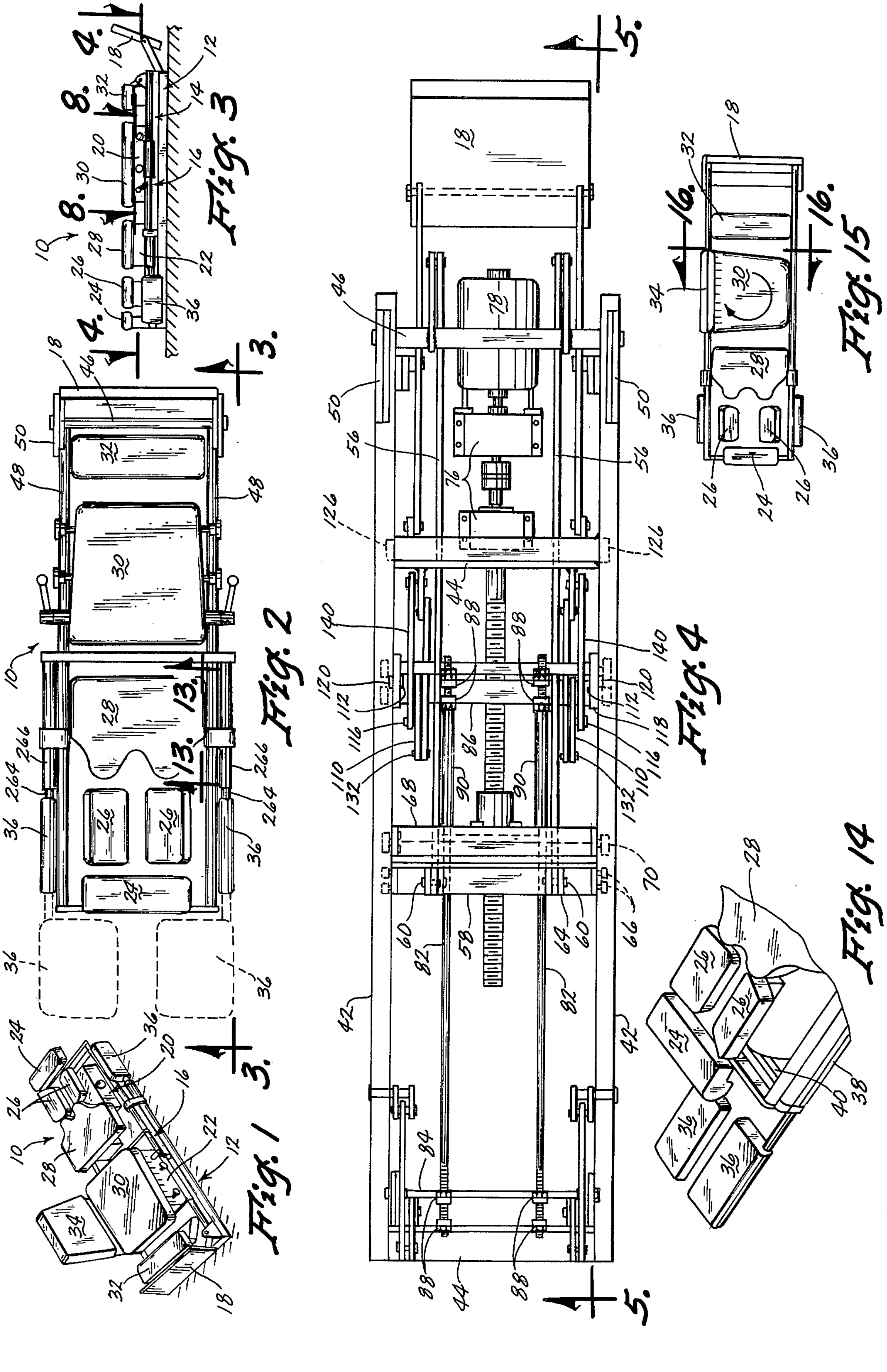
FIG. 1 is a perspective view of the chiropractic table of the present invention.
FIG. 2 is a top plan view thereof.
FIG. 3 is a sectional view taken along line 3—3 of FIG. 2.
FIG. 4 is a sectional view taken along line 4—4 of FIG. 3.
FIG. 14 is a partial pictorial view of the arm rest moved to the position, where they can be utilized as knee rests.
FIG. 15 is a top plan view of the chiropractic table of the present invention.

Referring to FIGS. 1-3, the numeral 10 generally designates the chiropractic table of the present invention. Table 10 comprises a pedestal frame 12, an intermediate frame 14, and a table frame 16. Mounted at one end of intermediate frame 14 is a foot base 18. Mounted above table frame 16 are an upper body support frame 20 and a lower body support frame 22. Upper body support frame 20 carries thereon a chest support piece 24, a pair of face or head support pieces 26, and a thoracic support piece 28. Lower body support frame 22 carries a pelvic support piece 30. Mounted at the foot of the table frame 16, is a tibial support piece 32. A cervical chair back 34 is mounted adjacent the edge of pelvic support piece 30. Also mounted along the sides of table frame 16 are a pair of arm supports 36, which are movable to form knee supports as will be described hereinafter.

Pedestal frame 12 is of a rectangular configuration having side frame members 38 (FIG. 5) which are interconnected at their opposite ends by cross members 40.

Intermediate frame 14 includes a pair of side frame members 42 (FIG. 4). Side frame members 42 are interconnected by means of a pair of cross frame members 44 and a transverse rotational shaft 46.

Table frame 16 is comprised of a pair of parallel bars 48 (FIG. 2). Each shaft 48 has at one of its ends an ear 50 which is welded or otherwise fixedly secured to rotatable shaft 46. Thus, rotation of shaft 46 causes pivotal movement of top frame 48 about shaft 46 from the position shown in FIG. 5 to the position shown in FIG. 7. Shaft 46 is rotatably journaled in a pair of upstanding ears 52 which are welded or otherwise fixed to intermediate frame 14.

Figures 5, 6, 7, 8, 8A:
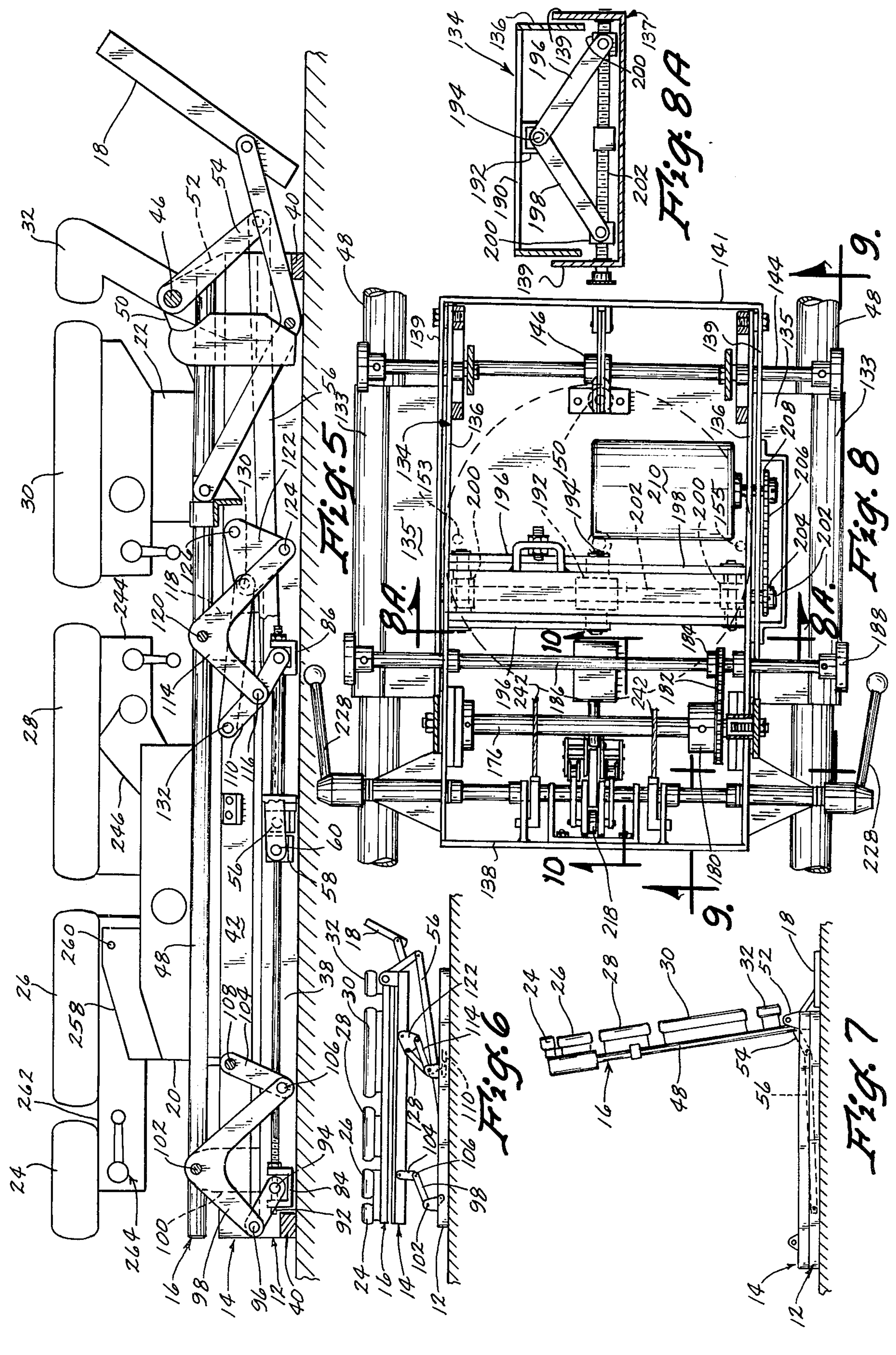
FIG. 5 is a sectional view taken along line 5—5 of FIG. 4.
FIG. 6 is a side elevational view similar to that shown in FIG. 3, but showing the device in its elevated position.
FIG. 7 is a view similar to FIG. 6, but showing the device in its tilted position.
FIG. 8 is an enlarged partial sectional view taken along line 8—8 of FIG. 3.
FIG. 8A is a reduced scale sectional view taken along line 8A—8A of FIG. 8.

A lever arm 54 is fixed to shaft 46 and extends downwardly therefrom as shown in FIGS. 5 and 7. Pivotally secured to the lower end of arm 54 is a tilt rod 56 which extends toward the head of the table and which is secured at its opposite end to a tilt rolling bar 58 (FIG. 4) by means of a pin 60. Rolling bar 58 includes a pair of spaced apart brackets 62, 64 for receiving pin 60. In addition, bar 58 includes a pair of roller bearings 66 at each end thereof rolling in a channel or track formed on the interior surface of side frame members 38 of pedestal frame 12. This permits rolling bar 58 to roll longitudinally along the length of pedestal frame 12. Referring to FIGS. 4, 5 and 6, if rolling bar 58 moves to the left, it causes tilt rod 56 to rotate transverse shaft 46 in a clockwise direction, thereby causing table frame 12 to rotate from a horizontal position such as shown in FIG. 5 to a near vertical position such as shown in FIG. 7. Rolling movement of bar 58 to the right as viewed in FIGS. 4, 5 and 7 permits the table frame to pivot downwardly to its original horizontal position.

The movement of tilt roll bar 58 is controlled by a master rolling bar 68. Master roll bar 68 includes rollers 70 which are also guided in the channel or track of pedestal frame 12. Master roll bar 68 includes a threaded collar 72 which is threaded over a lead screw 74. Lead screw 74 is connected by means of gear boxes and transmissions 76 to a motor 78. Actuation of motor 78 to rotate lead screw 74 in one direction causes master roll bar to move to the left as viewed in FIG. 4, thereby causing tilt roll bar 58 to also move to the left. Reversing the rotation of lead screw 74 moves master roll bar 68 to the right, and the weight of table frame 16 causes roll bar 58 to roll to the right in unison with master control bar 68. Thus, actuation of motor 78 permits controlling of the tilt action of table frame 16.

Master roll bar 68 is shown in its neutral position in FIG. 4. Movement to the left from that position causes raising of the table frame 16 to the position shown in FIG. 7 and returned to the neutral position shown in FIG. 4 permits table frame 16 to assume its horizontal position.

Master roller bar 68 also controls the means for elevating table frame 16 and intermediate frame 14 to the position shown in FIG. 6. This is accomplished by rotation of lead screw 74 so as to cause master roller bar 68 to move to the right from the position shown in FIG. 4. Master roller bar 68 has a pair of upstanding flanges 80, each of which have an opening extending therethrough. Extending through this opening are a pair of elevator rods 82. The opposite ends of elevator rods 82 are connected to a pair of spaced apart elevator roller bars 84, 86. Elevator roller 84, 86 are each provided with a plurality of upstanding flanges 88 for receiving the ends of tilt rods 82. The ends of tilt rods 82 are connected to roller bars 86 by means of nuts or other conventional fastening means. Mounted on elevator rods 82 between master roller bar 68 and elevator roller bar 86, are a pair of enlarged sleeves 90. These sleeves 90 are higher than the openings through upstanding flanges 80 or through upstanding flanges 88. Consequently, when master roller bar is in the position shown in FIG. 4, it abuts against sleeves 90, and these sleeves limit further movement of roller bar 68 towards roller bar 86. Consequently, when motor 78 is actuated to move to rotate lead screw 74 and move master roller bar 68 to the right from the position shown in FIG. 4, the abutting engagement of roller bar 68 with sleeves 90 causes movement to the right of both elevator roller bars 84, 86.

Each elevator roller bar is connected to a linkage which in turn interconnects pedestal frame 14 and intermediary frame 16. Referring to FIG. 5, elevator roller bar 84 is pivotally connected to the lower end of a lower link 92 for pivotal movement about an axis 94. The upper end of lower link 92 is pivotally connected about an axis 96 to one end of an L-shaped link 98. L-shaped link 98 is pivotally connected at its corner to an upstanding flange 100 for pivotal movement about an axis 102. Flange 100 is fixed to pedestal frame 12 so that the pivotal axis 102 for L-shaped link 98 is stationary with respect to pedestal frame 12. The other end of L-shaped link 98 is pivotally connected to an upper link 104 for pivotal movement about an axis 106. The upper end of upper link 104 is pivotally connected to intermediate frame 14 by means of a shaft 108.

The linkage for connecting elevator roller bar 86 to intermediate frame 14 is slightly different than the linkage previously described with respect to elevator roller bar 84. A slightly bent lower link 110 is pivotally connected at its lower end to elevator roller bar 86 about a pivotal axis 112. Link 110 is connected at its approximate center point to the lower end of an L-shaped link 114 for pivotal movement about an axis 116. L-shaped link 114 is connected at its L-shaped corner to an upstanding flange 118 for pivotal movement about an axis 120 in similar fashion to the pivotal axis 102 for L-shaped link 98. The opposite end of L-shaped link 114 is connected to a triangular link 112 for pivotal movement about an axis 124. Triangular link 122 is pivoted to intermediary frame 14 for pivotal movement about an axis 126. The third corner of triangular link 122 is pivotally connected to one end of a cross link 128 for pivotal movement about an axis 130. The opposite end of cross link 128 is connected to one end of bent link 110 for pivotal movement about an axis 132.

Table frame 16 and intermediate frame 14 are elevated with respect to pedestal frame by actuating motor 78 to turn lead screw 74 in such a manner as to move rolling master bar 68 to the right from the position shown in FIG. 4. The engagement of bar 68 with sleeves 56 causes movement of elevator roller bar 86 to the right as viewed in FIG. 4. Similarly, because elevator rods 82 interconnect elevator roller bars 84, 86, both of these roller bars move in unison.

Movement of elevator roller bars 84, 86 to the right causes pivotal movement of L-shaped links 98, 114 in a counterclockwise direction which in turn results in lifting of the intermediate frame 14 and table frame 16 to the position shown in FIG. 6. The linkages maintain intermediate frame 14 and table frame 16 in a horizontal position throughout the lifting action.

Referring to FIGS. 8–12, the lower body support frame 22 includes a pair of sleeves 133 which are interconnected by a web 135 and which are slidably mounted on parallel bars 48 of table frame 16 so as to permit longitudinal sliding movement thereon. Above web 135 is a yoke 137 having a pair of upstanding side walls 139 interconnected by a yoke web 140 and a rear vertical wall 141. Yoke web 140 is in facing relation with web 135 and is pivotally mounted thereto by a swivel 143 for pivotal movement about a vertical axis.

Embraced within sidewalls 139 of yoke 137 is a pelvic support box 134. Support box 134 has side walls 136, an end wall 138, and a bottom wall 145. Pelvic support box 134 includes adjacent the center thereof a cross bar 190 (FIGS. 8A and 9) having extending downwardly therefrom a stub 192. Pivotally extending through stub 192 is a pivot shaft 194 which also serves as a pivotal connection for two pairs of support lengths 196, 198. Support links 196, 198 are pivotally mounted at their outer ends to a pair of threaded collars 200 which are threaded on a lead screw 202 rotatably mounted to lower body support frame 22. Lead screw 202 is threaded in such a manner that rotation thereof causes threaded collars 200 to move either towards the longitudinal center of lead screw 202 or towards the opposite ends of lead screw 202, thereby causing the raising and lowering of the pivot point 194 and consequently the raising or lowering of box 134.

One end of lead screw 202 has a sprocket 204 thereon for receiving a chain 206 which is in turn trained over a sprocket 208 driven by a motor 210. Thus the actuation of motor 210 causes the raising or lowering of box 134 with respect to lower body support 22.

Figure 9:
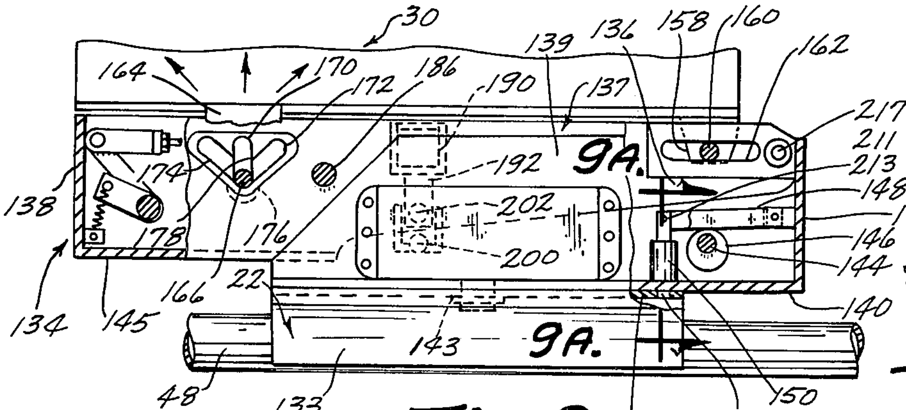
FIG. 9 is a sectional view taken along line 9—9 of FIG. 8.
Figure 9A:
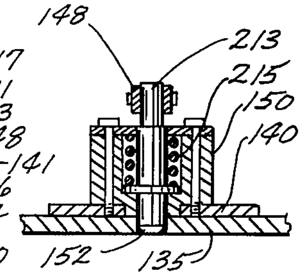
FIG. 9A is a sectional view taken along line 9A—9A of FIG. 9.
Figure 10:
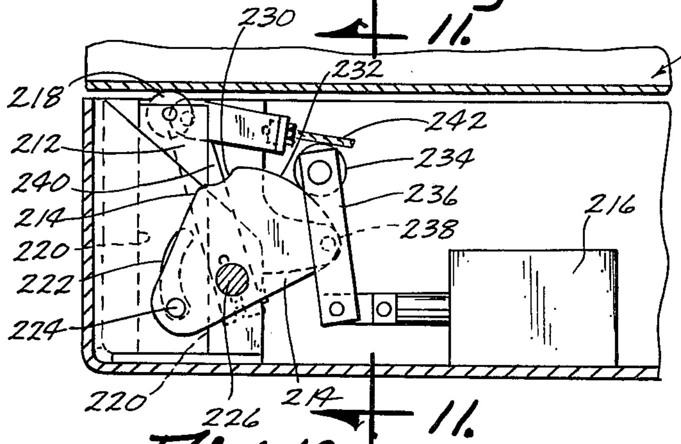
FIG. 10 is a sectional view taken along line 10—10 of FIG. 8.
Figure 11:
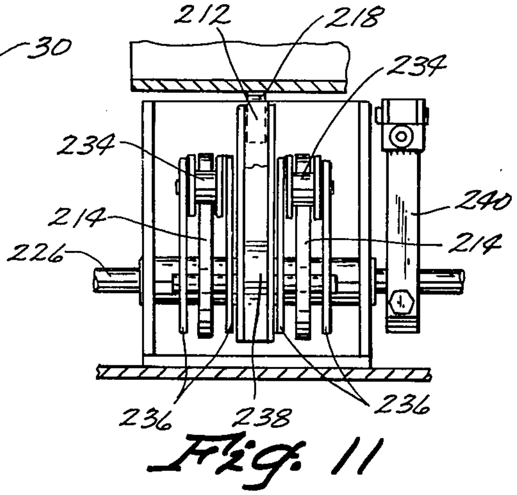
FIG. 11 is a sectional view taken along line 11—11 of FIG. 10.

Referring to FIG. 9, the right hand end of box 134 is pivotally mounted to yoke 137 by means of ears 211 which are rotatable on horizontal shafts 217 attached to sidewalls 139 of yoke 137, thus raising or lowering the forward end of box 134 by means of motor 210 causes pivotal movement of box 134 about shafts 217.

Means for controlling the pivotal movement of yoke 137 about swivel 143 are provided by a cam shaft 144, and a cam 146, which engages a link 148. Link 148 is pivotally connected at one of its ends to end wall 141 of yoke 137 and is pivotally connected at the other of its ends to a plunger 213 which is vertically slidably received within a collar 150 mounted in the yoke web 140 of yoke 137. Plunger 213 is spring mounted by means of a spring 215 so as to be urged in a downward position and the lower tip of plunger 213 is adapted to be retentively fitted within a detent hole 152 in web 135 of lower body support 22. Because spring 215 urges plunger 213 downwardly in a normal position, the tendency is for plunger 213 to engage detent hole 152 and thereby lock yoke 137 against pivotal movement about swivel 143.

However, cam 146 limits the downward movement of plunger 213. By rotating shaft 144 it is possible to therefore lift plunger 213 out of detent hole 152 to permit rotation of yoke 137. Two other detent holes, 153, 155 (FIG. 8) are provided in web 135 for locking yoke 137 in various other positions.

Pelvic support piece 30 includes at one end a downwardly projecting flange 158 having a pin 160 slidably received in a horizontal slot 162 in side wall 136 of box 134. This permits pelvic support piece 30 to move longitudinally with respect to box 134, but prevents the pin 160 from moving vertically in slot 162.

Adjacent the opposite end of pelvic piece 30 from pin 160 is another downwardly projecting flange 164 having a pin 166 projecting through a three way slot 168 having a vertical portion 170 and two angular portions 172, 174. Thus, flange 164 may move upwardly in vertical slot 170 or in either of angular slots 172, 174. Pin 166 also rests at its inner end in a slotted shaft 176 having a slot 178 therein.

As can best be seen in FIG. 8, shaft 176 has a sprocket 180 thereon. A chain 182 is trained around this sprocket and the corresponding sprocket 184 on another shaft 186 which has a handle 188 for grasping and turning. Rotation of shaft 186 causes rotation of shaft 176, and therefore causes slot 178 to move into alignment with vertical slot 170, or with either angular slot 172, 174, whichever is desired. As can be seen in FIG. 9, movement of slot 178 into alignment with any one of slots 170, 172, and 174 forecloses the possibility that pin 166 can move to any slot other than the one with which slot 178 is aligned. This provides means for selecting the particular angle at which pelvic support piece 30 may be elevated with respect to box 134.

The cock and drop feature for pelvic support piece 30 is provided by a sliding support member 212, a cam 214, and a solenoid 216 (FIGS. 8–12). Sliding support member 212 includes at its upper end a roller 218 which is adapted to engage the under surface of pelvic support piece 30. Sliding support member 212 is vertically slidably movable in a vertical slot 220. Formed in the side walls of slot 220 is an arcuate opening 222 through which extends a shaft 224 which engages the lower end of sliding support member 212. Shaft 224 has connected to its opposite end a pair of cams 214. Cams 214 are keyed to a transversely extending axle 226 which is rotatably mounted to box 134. The opposite ends of axle 226 have lever handles 228 mounted thereon for permitting the chiropractor to manually rotate axle 226. Rotation of axle 226 causes cam 214 to also rotate, thereby raising and lowering shaft 224 and slide support member 212. Thus, the raising and lowering of pelvic support piece 30 is controlled by manual operation of lever handles 228.

Cam 214 includes a notch 230 therein and further includes an arcuate cam surface 232. Engaging cam surface 232 for rolling engagement thereon is a cam follower roller 234 which is mounted at the upper ends of a pair of cam follower links 236. Links 236 are pivotally mounted at their centers to a central support plate 238 which is fixed with respect to box 234. The lower end of links 236 are connected to solenoid 216. Thus, actuation of solenoid 216 causes rotation of links 236 in such a manner to increase the pressure of roller 234 against cam surface 232.

Figure 12:
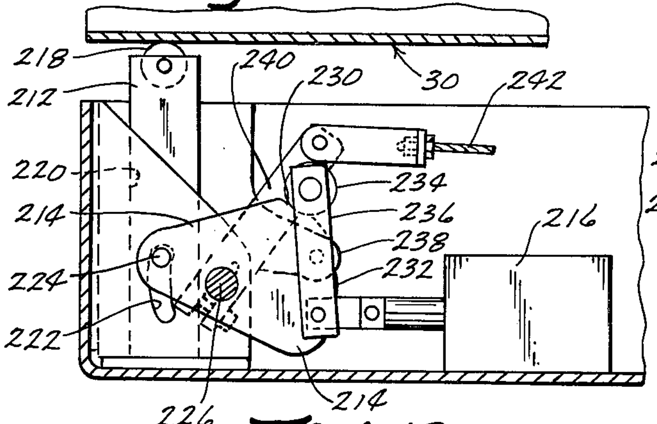
FIG. 12 is a sectional view similar to FIG. 10, but showing the cock and drop mechanism in its elevated position.
Figure 13:
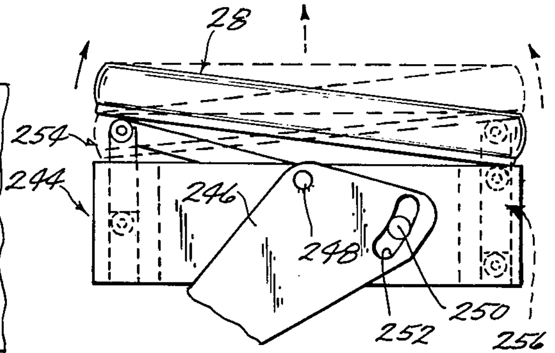
FIG. 13 is a sectional view taken along line 13—13 of FIG. 2.

In operation, the chiropractor depresses lever handles 228 to raise pelvic support piece 30 to its elevated cocked position as shown in FIG. 12. As can be seen from FIG. 12, roller 234 enters and is retained in notch 230 of cam 214 when the support piece 30 is in its cocked position. Actuation of solenoid 216 causes roller 234 to be retained in notch 230 and thereby prevents the lowering of pelvic support piece 30 in response to the weight of the patient. The strength of solenoid 216 is chosen so that it will yield in response to a predetermined pressure. Thus, in treating the patient the chiropractor exerts downward pressure on the patient and consequently causes a resultant downward pressure through support member 212, cam 214, and roller 234. When the pressure becomes sufficiently great to overcome the strength of solenoid 216, solenoid 216 gives and roller 234 rolls out of notch 30, thereby causing the support piece 30 to drop to its original position shown in FIG. 10.

As an alternative to manual cocking of pelvic support piece 30, it is possible to utilize a pair of levers 240 which are keyed to axle 226 (FIGS. 8, 10 and 11), and which are connected to a cable 242. Cable 242 may be connected to any type of power means such as a winch, a hydraulic system or other conventional means. This will permit a power means for lifting support piece 30 rather than utilizing manual means.

Thoracic support piece 28 is supported by a thoracic support box 244. Thoracic support box 244 is mounted to an upwardly extending plate 246 which is rigidly secured to upper body support frame 20. Plate 246 has a pivot shaft 248 which extends through thoracic support box 244 and provides a pivotal securement thereof. A locking handle 250 extends through an arcuate slot 252 in plate 246 and may be tightened to hold thoracic support box 244 in the desired position.

Thoracic support piece 28 is supported by thoracic support box 244 by means of two cock and drop assemblies designated generally by the numerals 254,256. These assemblies are substantially the same construction as the cock and drop assembly shown for the pelvic support piece. Since each of these assemblies 254,256 are located at opposite ends of thoracic support piece 28, it is possible to cock each of them independently or together to achieve the desired results. When the cock and drop assemblies are used the thoracic support box is held in a fixed position by locking handle 250 and not allowed to swing.

Extending upwardly from upper body support frame 20 are a pair of spaced apart plates 258. Pivotally mounted to these plates by means of shaft 260 is a head and chest box 262. Mechanism (not shown) is provided for pivotal adjustment of box 262 about axis 260. A cock and drop mechanism 264 (FIG. 5) similar to that utilized in the pelvic and thoracic pieces, is provided for cocking and dropping the chest and head pieces 24, 26 in unison as they pivot in unison about axis 260.

Referring to FIG. 2, arm supports 36 are mounted to shafts 264 which are telescoped within sleeves 266. For use as arm rests, the chiropractor merely rotates rests 36 about shaft 264, so that they lie in a horizontal plane. The patient can then place his arm on these rests.

On occasion, the chiropractor may wish the patient to kneel and lean over chest piece 24. In this situation, arm rests 36 are telescoped out to the position shown by shadow lines in FIG. 2. They are then rotated so as to provide knee supports for the patient while the patient kneels.

Figure 16:
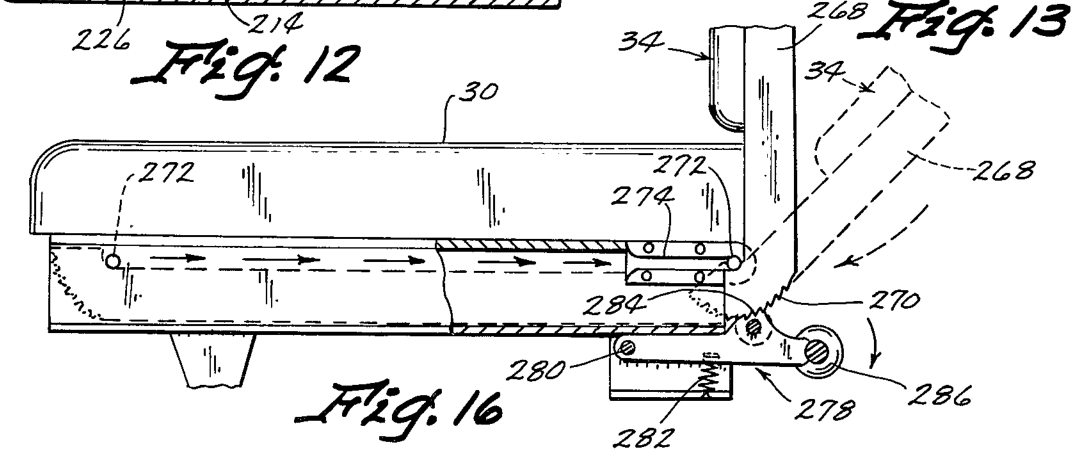
FIG. 16 is a sectional view taken along line 16—16 of FIG. 15.

It also may be desirable for the patient to sit on the table. For this purpose, a cervical chair is provided by cervical chair back 34. As can be seen in FIG. 16, chair back 34 includes side frame members 268 which have arcuate ratchet surfaces 270 at the lower end thereof. During non-use, cervical support 34 can slide beneath pelvic support piece 30. When it is desired to use cervical support 34, the chiropractor slides it out from beneath pelvic support piece 30. A pin 272 catches in a U-shaped slot 274 and thereby provides a pivotal hinge for cervical chair back 34. A pawl 278 is pivotally mounted for pivotal movement about axis 280 and is spring mounted by spring 282 into upward engagement with ratchets 270. Pawl 278 has a corresponding ratchet surface 284 for engaging ratchets 270. Thus, chair support back 34 may be locked into any desired position from the vertical position shown in solid lines in FIG. 16 to other angular positions such as the one shown in shadow lines in FIG. 16. A roller 286 is provided for facilitating the movement of the chair back to its stored position.

From the foregoing, it can be seen that the present invention accomplishes at least all of its stated objectives. The chiropractor table may be elevated to any desired position. It may also be tilted to any desired position. The cock and drop features of the various support pieces greatly facilitate the treatment provided by the chiropractor. The arm rests may be converted to knee pads, and the cervical chair provides added flexibility. Certain variations may be utilized without detracting from the invention. For example lead screw 74 may be replaced by a hydraulic cylinder and power source 78 may be replaced by a hydraulic pump or electric motor. The cocking action of the cock and drop assemblies may be accomplished by hydraulic cylinders with hydraulic valves in the place of solenoids. Thus, it can be seen that the device accomplishes at least all of its stated objectives.

What is claimed is:

1. A chiropractic table comprising:

an elongated table frame, a plurality of support pieces positioned in spaced relation along the length of said table and each having an upwardly presented support surface, mounting means for mounting at least one of said support pieces to said frame for vertical movement between upper and lower positions;

a vertically movable member mounted to said table frame for vertical movement with respect thereto, and being in supporting engagement with said one support piece;

a rotatable cam mounted to said frame for pivotal movement about a horizontal axis, said cam having first and second ends on opposite sides of said axis, said first end engaging said vertically movable member for lifting thereof in response to rotational movement of said cam in one direction and for lowering thereof in response to rotation of said cam in the opposite direction;

said second end of said cam having a cam surface comprising a curved surface and a notch, a cam follower in rolling engagement with said cam surface and adapted to roll into said notch when said vertically movable member is in a predetermined upper position;

yieldable power means connected to said cam follower for urging said cam follower toward said notch with a force of predetermined magnitude and being yieldable to permit said cam follower to roll out of said notch in response to a moment of predetermined magnitude exerted on said cam by a downward force acting through said support piece and vertically movable member.

2. A chiropractic table according to claim 9 wherein said mounting means comprises a body support assembly mounted to said table for longitudinal movement thereon, first connecting means pivotally connecting a first end of said one support piece to said body support assembly and permitting limited longitudinal movement of said one support piece with respect to said body support assembly; said one support piece having a second end supported by said vertically movable member.

3. A chiropractic table according to claim 10 wherein said support assembly includes a guide slot having a plurality of slot segments therein, said second end of said support piece having a pin extending into said slot, a slotted shaft having a pin receiving slot therein which also receives said pin of said support piece, said slotted shaft being movably mounted to said support assembly for selective movement to a predetermined number of positions to present said pin adjacent various segments of said guide slot and to prevent said pin from entering all but one of said segments.

* * * * *